United States Patent
West et al.

(10) Patent No.: US 8,870,828 B2
(45) Date of Patent: Oct. 28, 2014

(54) PHLEBOTOMY NEEDLE ASSEMBLY AND FRANGIBLE COVER

(71) Applicant: Fenwal, Inc., Lake Zurich, IL (US)

(72) Inventors: Richard L. West, Lake Villa, IL (US);
Daniel R. Lynn, Spring Grove, IL (US);
Mark B. Jones, Libertyville, IL (US);
Daniel F. Bischof, Bull Valley, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 13/693,189

(22) Filed: Dec. 4, 2012

(65) Prior Publication Data

US 2013/0096462 A1    Apr. 18, 2013

Related U.S. Application Data

(62) Division of application No. 12/013,844, filed on Jan. 14, 2008, now Pat. No. 8,323,251.

(51) Int. Cl.
| | |
|---|---|
| *A61M 5/32* | (2006.01) |
| *B65D 85/46* | (2006.01) |
| *A61B 5/15* | (2006.01) |
| *A61M 5/31* | (2006.01) |

(52) U.S. Cl.
CPC ......... *A61B 5/150541* (2013.01); *A61B 5/1405* (2013.01); *A61M 5/3202* (2013.01); *A61M 2005/312* (2013.01)
USPC .......................................... 604/192; 206/365

(58) Field of Classification Search
USPC ........................ 604/110, 111, 192, 198, 263
See application file for complete search history.

(56) References Cited

U.S. PATENT DOCUMENTS

| | | | | | |
|---|---|---|---|---|---|
| 2,076,121 | A | * | 4/1937 | Dickinson | 604/242 |
| 2,702,037 | A | * | 2/1955 | Walter | 604/272 |
| 2,716,983 | A | * | 9/1955 | Ryan et al. | 604/274 |
| 2,727,514 | A | * | 12/1955 | Lockhart | 604/242 |
| 3,073,307 | A | * | 1/1963 | Stevens | 604/192 |

(Continued)

FOREIGN PATENT DOCUMENTS

| | | |
|---|---|---|
| EP | 1 221 303 A2 | 7/2001 |
| EP | 1 340 458 A1 | 9/2003 |
| EP | 1 506 791 A1 | 2/2005 |
| EP | 1 665 986 A1 | 11/2005 |

OTHER PUBLICATIONS

Partial Search Report for European Patent Application No. 09004481.9, Mar. 7, 2009.

(Continued)

*Primary Examiner* — Kevin C Sirmons
*Assistant Examiner* — William Carpenter
(74) *Attorney, Agent, or Firm* — Cook Alex Ltd.

(57) ABSTRACT

Medical needle assemblies incorporating a needle cover are provided. According to one aspect, the needle cover is integrally formed from a material that: (1) is sufficiently rigid to prevent bending of an underlying cannula, (2) is suitable for allowing a frangible portion thereof to be broken under preselected conditions, and/or (3) has a moisture vapor transmission rate sufficient for steam sterilization of a needle tip enclosed by the needle cover. According to another aspect, at least part of a cap portion and a hub portion of the needle cover are translucent. According to yet another aspect, the needle cover is provided with a wing having an enlarged rib suitable for gripping during separation of a cap portion from the remainder of the needle cover.

18 Claims, 5 Drawing Sheets

(56) References Cited

U.S. PATENT DOCUMENTS

| | | | |
|---|---|---|---|
| 3,330,278 A * | 7/1967 | Santomieri | 604/161 |
| 3,523,530 A | 8/1970 | Pagones et al. | |
| 3,640,275 A | 2/1972 | Burke et al. | |
| 4,013,080 A | 3/1977 | Froning | |
| 4,078,565 A | 3/1978 | Genese | |
| 4,129,128 A | 12/1978 | McFarlane | |
| 4,194,504 A | 3/1980 | Harms et al. | |
| 4,233,974 A | 11/1980 | Desecki et al. | |
| 4,240,427 A | 12/1980 | Akhavi | |
| 4,250,880 A | 2/1981 | Gordon | |
| 4,300,553 A | 11/1981 | Seberg | |
| 4,352,354 A | 10/1982 | Ujihara | |
| D269,549 S * | 6/1983 | Gross | D24/112 |
| 4,388,074 A | 6/1983 | Seberg et al. | |
| 4,402,682 A | 9/1983 | Garver, Sr. et al. | |
| 4,405,307 A | 9/1983 | Taylor | |
| 4,413,992 A | 11/1983 | Soika | |
| 4,435,175 A | 3/1984 | Friden | |
| 4,435,177 A * | 3/1984 | Kuhlemann et al. | 604/263 |
| 4,445,893 A | 5/1984 | Bodicky | |
| 4,484,913 A | 11/1984 | Swauger | |
| 4,496,352 A | 1/1985 | Soika | |
| 4,508,534 A | 4/1985 | Garver, Sr. et al. | |
| 4,530,697 A * | 7/1985 | Kuhlemann et al. | 604/263 |
| 4,551,138 A | 11/1985 | Shinohara | |
| 4,563,177 A | 1/1986 | Kamen | |
| D283,053 S * | 3/1986 | Hermann | D24/129 |
| 4,574,456 A * | 3/1986 | Soika | 29/451 |
| 4,585,444 A | 4/1986 | Harris | |
| 4,627,842 A | 12/1986 | Katz | |
| 4,657,535 A * | 4/1987 | Nishimura et al. | 604/263 |
| 4,690,675 A | 9/1987 | Katz | |
| 4,698,057 A | 10/1987 | Joishy | |
| 4,720,285 A * | 1/1988 | Pickhard | 604/192 |
| 4,834,708 A | 5/1989 | Pillari | |
| 4,888,001 A | 12/1989 | Schoenberg | |
| 4,909,788 A | 3/1990 | Egolf | |
| 4,938,744 A | 7/1990 | Wharff et al. | |
| 4,938,745 A | 7/1990 | Sagstetter | |
| 4,941,881 A | 7/1990 | Masters et al. | |
| 4,964,854 A * | 10/1990 | Luther | 604/166.01 |
| 4,966,589 A | 10/1990 | Kaufman | |
| 5,024,665 A | 6/1991 | Kaufman | |
| 5,085,647 A | 2/1992 | Henderson | |
| 5,112,311 A | 5/1992 | Utterberg et al. | |
| 5,112,312 A | 5/1992 | Luther | |
| 5,127,910 A | 7/1992 | Talonn et al. | |
| 5,141,497 A | 8/1992 | Erskine | |
| 5,152,755 A | 10/1992 | Yoshinori | |
| 5,156,599 A | 10/1992 | Ranford et al. | |
| 5,169,391 A | 12/1992 | Vogel | |
| 5,169,392 A | 12/1992 | Ranford et al. | |
| 5,197,953 A | 3/1993 | Colonna | |
| 5,266,072 A | 11/1993 | Utterberg et al. | |
| 5,267,971 A | 12/1993 | Brimhall | |
| 5,279,581 A | 1/1994 | Firth et al. | |
| 5,290,265 A | 3/1994 | Davis et al. | |
| 5,297,561 A | 3/1994 | Hulon | |
| 5,304,144 A | 4/1994 | Brimhall | |
| 5,306,253 A | 4/1994 | Brimhall | |
| 5,314,441 A | 5/1994 | Cusack et al. | |
| 5,322,514 A | 6/1994 | Steube et al. | |
| 5,328,466 A | 7/1994 | Demark | |
| 5,336,191 A | 8/1994 | Davis et al. | |
| 5,336,197 A | 8/1994 | Kuracina et al. | |
| 5,354,282 A | 10/1994 | Bierman | |
| 5,382,240 A | 1/1995 | Lam | |
| 5,385,554 A | 1/1995 | Brimhall | |
| 5,413,562 A | 5/1995 | Swauger | |
| 5,433,703 A | 7/1995 | Utterberg et al. | |
| 5,449,349 A | 9/1995 | Sallee et al. | |
| 5,456,671 A | 10/1995 | Bierman | |
| 5,466,225 A | 11/1995 | Davis et al. | |
| 5,498,241 A | 3/1996 | Fabozzi | |
| 5,538,353 A | 7/1996 | DeHavilland | |
| 5,540,666 A * | 7/1996 | Barta et al. | 604/192 |
| 5,558,651 A | 9/1996 | Crawford et al. | |
| 5,571,091 A | 11/1996 | Davis et al. | |
| 5,578,013 A | 11/1996 | Bierman | |
| 5,591,138 A | 1/1997 | Vaillancourt | |
| 5,647,849 A | 7/1997 | Kalin | |
| 5,669,882 A | 9/1997 | Pyles | |
| 5,674,201 A | 10/1997 | Steinman | |
| 5,702,371 A | 12/1997 | Bierman | |
| 5,704,917 A | 1/1998 | Utterberg | |
| 5,722,959 A | 3/1998 | Bierman | |
| 5,725,504 A | 3/1998 | Collins | |
| 5,743,888 A | 4/1998 | Wilkes et al. | |
| 5,776,106 A | 7/1998 | Matyas | |
| 5,800,400 A | 9/1998 | Hogan | |
| 5,827,230 A | 10/1998 | Bierman | |
| 5,833,667 A | 11/1998 | Bierman | |
| 5,885,251 A | 3/1999 | Luther | |
| 5,910,133 A | 6/1999 | Gould | |
| 5,911,707 A | 6/1999 | Wolvek et al. | |
| 5,928,199 A | 7/1999 | Nakagami | |
| 5,944,695 A | 8/1999 | Johnson et al. | |
| 5,944,699 A | 8/1999 | Barrelle et al. | |
| 5,980,495 A | 11/1999 | Heinz et al. | |
| 6,068,148 A | 5/2000 | Weiler | |
| 6,077,244 A | 6/2000 | Botich et al. | |
| 6,113,577 A | 9/2000 | Hakky et al. | |
| 6,149,629 A | 11/2000 | Wilson et al. | |
| 6,193,696 B1 | 2/2001 | Jansen et al. | |
| 6,193,706 B1 | 2/2001 | Thorud et al. | |
| RE37,110 E | 3/2001 | Hollister | |
| 6,196,998 B1 | 3/2001 | Jansen et al. | |
| 6,217,550 B1 | 4/2001 | Capes | |
| 6,217,561 B1 | 4/2001 | Gibbs | |
| 6,224,571 B1 | 5/2001 | Bierman | |
| 6,231,548 B1 | 5/2001 | Bassett | |
| RE37,252 E | 7/2001 | Hollister | |
| 6,290,676 B1 | 9/2001 | Bierman | |
| 6,298,541 B1 | 10/2001 | Newby et al. | |
| 6,302,866 B1 | 10/2001 | Marggi | |
| 6,309,543 B1 | 10/2001 | Fenton et al. | |
| 6,375,640 B1 | 4/2002 | Teraoka | |
| 6,425,887 B1 | 7/2002 | McGuckin et al. | |
| 6,428,515 B1 | 8/2002 | Bierman et al. | |
| 6,436,086 B1 | 8/2002 | Newby et al. | |
| 6,440,104 B1 | 8/2002 | Newby et al. | |
| 6,482,180 B2 | 11/2002 | Toyokawa et al. | |
| 6,500,155 B2 | 12/2002 | Sasso | |
| 6,517,522 B1 | 2/2003 | Bell et al. | |
| 6,520,938 B1 | 2/2003 | Funderburk et al. | |
| 6,524,279 B1 | 2/2003 | Shields | |
| 6,537,255 B1 | 3/2003 | Raines | |
| 6,551,284 B1 | 4/2003 | Greenberg et al. | |
| 6,558,353 B2 | 5/2003 | Zohmann | |
| 6,582,397 B2 | 6/2003 | Alesi et al. | |
| 6,616,635 B1 | 9/2003 | Bell et al. | |
| 6,620,136 B1 | 9/2003 | Pressly, Sr. et al. | |
| 6,629,957 B1 * | 10/2003 | Wiklund | 604/192 |
| 6,638,256 B2 | 10/2003 | Jansen et al. | |
| 6,673,046 B2 | 1/2004 | Bierman et al. | |
| 6,682,348 B2 | 1/2004 | Lawter et al. | |
| 6,695,814 B2 | 2/2004 | Greene et al. | |
| 6,770,055 B2 | 8/2004 | Bierman et al. | |
| 6,786,892 B2 | 9/2004 | Bierman | |
| 6,827,705 B2 | 12/2004 | Bierman | |
| 6,827,707 B2 | 12/2004 | Wright et al. | |
| 6,837,875 B1 | 1/2005 | Bierman | |
| 6,837,877 B2 | 1/2005 | Zurcher | |
| 6,840,920 B2 | 1/2005 | Millerd | |
| 6,846,302 B2 | 1/2005 | Shemesh et al. | |
| 6,880,801 B2 | 4/2005 | Matkovich et al. | |
| 6,881,202 B2 | 4/2005 | Coleman et al. | |
| 6,905,483 B2 | 6/2005 | Newby et al. | |
| 6,911,020 B2 | 6/2005 | Raines | |
| 6,921,388 B2 | 7/2005 | Swenson | |
| 6,932,803 B2 | 8/2005 | Newby | |
| 6,951,550 B2 | 10/2005 | Bierman | |
| 6,966,897 B2 | 11/2005 | Shimazaki | |
| 6,979,320 B2 | 12/2005 | Bierman | |

(56) References Cited

U.S. PATENT DOCUMENTS

| | | |
|---|---|---|
| 6,984,223 B2 | 1/2006 | Newby et al. |
| RE38,996 E | 2/2006 | Crawford et al. |
| 6,997,902 B2 | 2/2006 | Thorne et al. |
| 6,997,913 B2 | 2/2006 | Wilkinson |
| 7,014,627 B2 | 3/2006 | Bierman |
| 7,032,590 B2 | 4/2006 | Loeffler et al. |
| 7,041,085 B2 | 5/2006 | Perez et al. |
| 7,048,718 B1 | 5/2006 | Mithiue et al. |
| 7,070,587 B2 | 7/2006 | Meier et al. |
| 7,083,600 B2 | 8/2006 | Meloul |
| 7,090,191 B2 | 8/2006 | Matkovich et al. |
| 7,112,190 B2 | 9/2006 | Bressler et al. |
| 7,112,191 B2 | 9/2006 | Daga |
| 7,125,397 B2 | 10/2006 | Woehr et al. |
| 7,144,387 B2 | 12/2006 | Millerd |
| 7,153,291 B2 | 12/2006 | Bierman |
| 7,155,287 B2 | 12/2006 | Gavronsky |
| 7,201,742 B2 | 4/2007 | Popovsky |
| 7,294,118 B2 | 11/2007 | Saulenas et al. |
| 7,306,576 B2 | 12/2007 | Hongo et al. |
| 7,316,668 B2 | 1/2008 | Swenson |
| 2001/0041866 A1 | 11/2001 | Capes et al. |
| 2002/0007147 A1 | 1/2002 | Capes et al. |
| 2002/0072715 A1 | 6/2002 | Newby et al. |
| 2003/0144631 A1 | 7/2003 | Doyle et al. |
| 2003/0163096 A1 | 8/2003 | Swenson et al. |
| 2003/0181869 A1 | 9/2003 | Swenson et al. |
| 2003/0181870 A1 | 9/2003 | Bressler et al. |
| 2003/0181871 A1 | 9/2003 | Wilkinson et al. |
| 2004/0039334 A1 | 2/2004 | Li |
| 2004/0049159 A1 | 3/2004 | Barrus et al. |
| 2004/0068242 A1 | 4/2004 | McGuckin, Jr. |
| 2004/0092872 A1 | 5/2004 | Botich et al. |
| 2004/0116874 A1 | 6/2004 | Lourenco et al. |
| 2004/0186434 A1 | 9/2004 | Harding et al. |
| 2004/0186440 A1 | 9/2004 | Jansen et al. |
| 2004/0199124 A1 | 10/2004 | Conte |
| 2004/0220533 A1 | 11/2004 | Caizza et al. |
| 2004/0249346 A1 | 12/2004 | Kunitomi et al. |
| 2005/0033242 A1 | 2/2005 | Perez et al. |
| 2005/0054987 A1 | 3/2005 | Perez et al. |
| 2005/0070849 A1 | 3/2005 | Yang |
| 2005/0075610 A1 | 4/2005 | Bierman |
| 2005/0090783 A1 | 4/2005 | Sibbitt, Jr. |
| 2005/0101914 A1 | 5/2005 | Shue et al. |
| 2005/0148931 A1 | 7/2005 | Juhasz |
| 2005/0148993 A1 | 7/2005 | Mathias et al. |
| 2005/0177112 A1 | 8/2005 | Restelli et al. |
| 2005/0251092 A1 | 11/2005 | Howell et al. |
| 2005/0277881 A1 | 12/2005 | Sibbitt, Jr. |
| 2005/0277895 A1 | 12/2005 | Giambattista et al. |
| 2005/0283115 A1 | 12/2005 | Giambattista et al. |
| 2006/0064061 A1 | 3/2006 | Solomon et al. |
| 2006/0089599 A1 | 4/2006 | Lynn et al. |
| 2006/0089601 A1 | 4/2006 | Dionigi |
| 2006/0100588 A1 | 5/2006 | Brunnberg et al. |
| 2006/0184127 A1 | 8/2006 | Bierman |
| 2006/0184129 A1 | 8/2006 | Bierman |
| 2006/0217669 A1 | 9/2006 | Botha |
| 2006/0247577 A1 | 11/2006 | Wright |
| 2006/0264836 A1 | 11/2006 | Bierman |
| 2006/0270994 A1 | 11/2006 | Bierman |
| 2006/0270995 A1 | 11/2006 | Bierman |
| 2007/0060840 A1 | 3/2007 | Conway |
| 2007/0066937 A1 | 3/2007 | Jones et al. |
| 2007/0066958 A1 | 3/2007 | Wright |
| 2007/0088272 A1 | 4/2007 | Jones et al. |
| 2007/0093760 A1 | 4/2007 | Wexler |
| 2007/0100296 A1 | 5/2007 | Hwang |
| 2007/0135769 A1 | 6/2007 | Tollini |
| 2007/0149930 A1 | 6/2007 | Bierman |
| 2007/0173768 A2 | 7/2007 | Bierman |
| 2007/0239118 A1 | 10/2007 | Ono et al. |
| 2007/0244441 A1 | 10/2007 | Abbott |
| 2007/0250014 A1 | 10/2007 | Utterberg et al. |
| 2007/0265571 A1 | 11/2007 | Utterberg et al. |
| 2007/0270758 A1 | 11/2007 | Hanner et al. |
| 2007/0276333 A1 | 11/2007 | Bierman |
| 2007/0287963 A1 | 12/2007 | Bierman |
| 2008/0004573 A1 | 1/2008 | Kaufmann et al. |

OTHER PUBLICATIONS

Office Action for U.S. Appl. No. 12/013,844, dated Oct. 16, 2009.
Office Action for U.S. Appl. No. 12/013,844, dated Mar. 23, 2010.
Office Action for U.S. Appl. No. 12/013,844, dated Oct. 4, 2010.
Office Action for U.S. Appl. No. 12/013,844, dated Feb. 28, 2011.
Extended Search Report for European Patent Application No. 09004481.9.

* cited by examiner

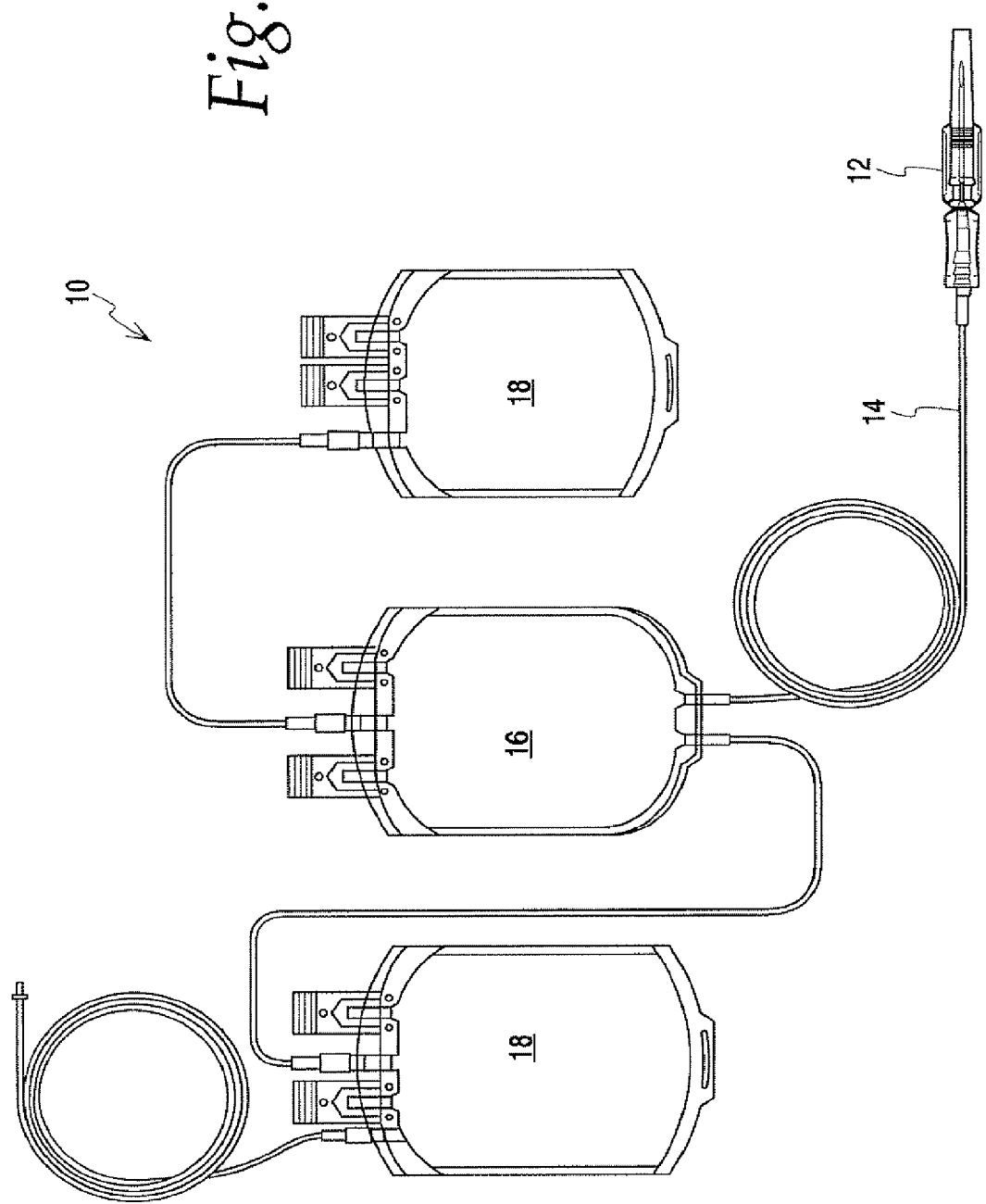

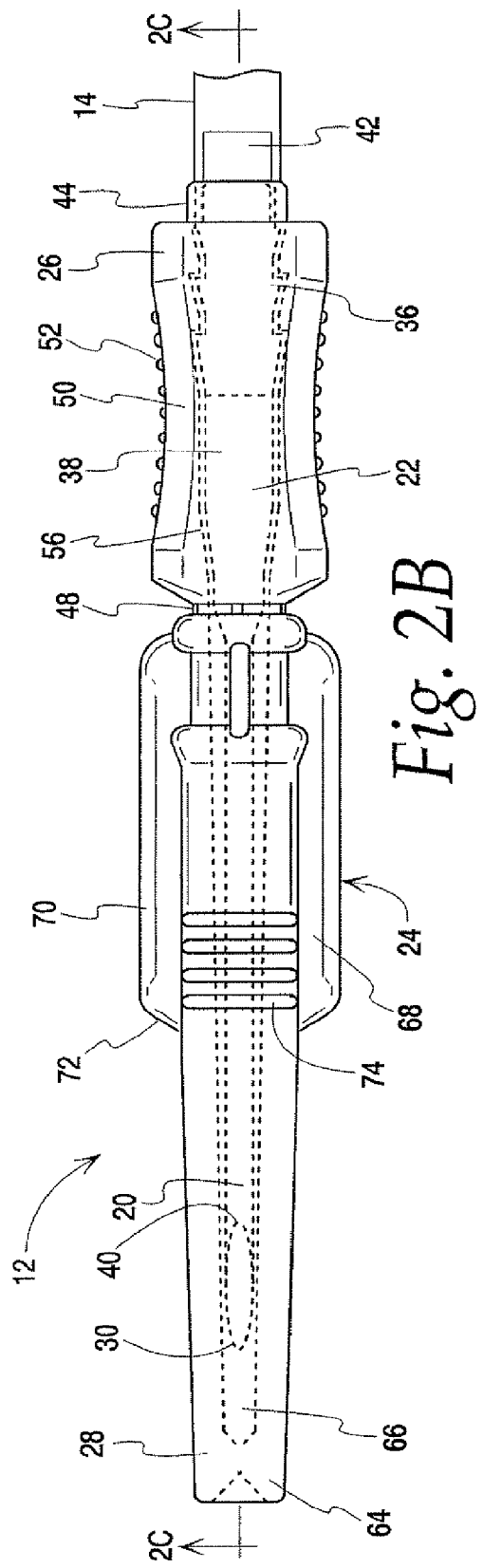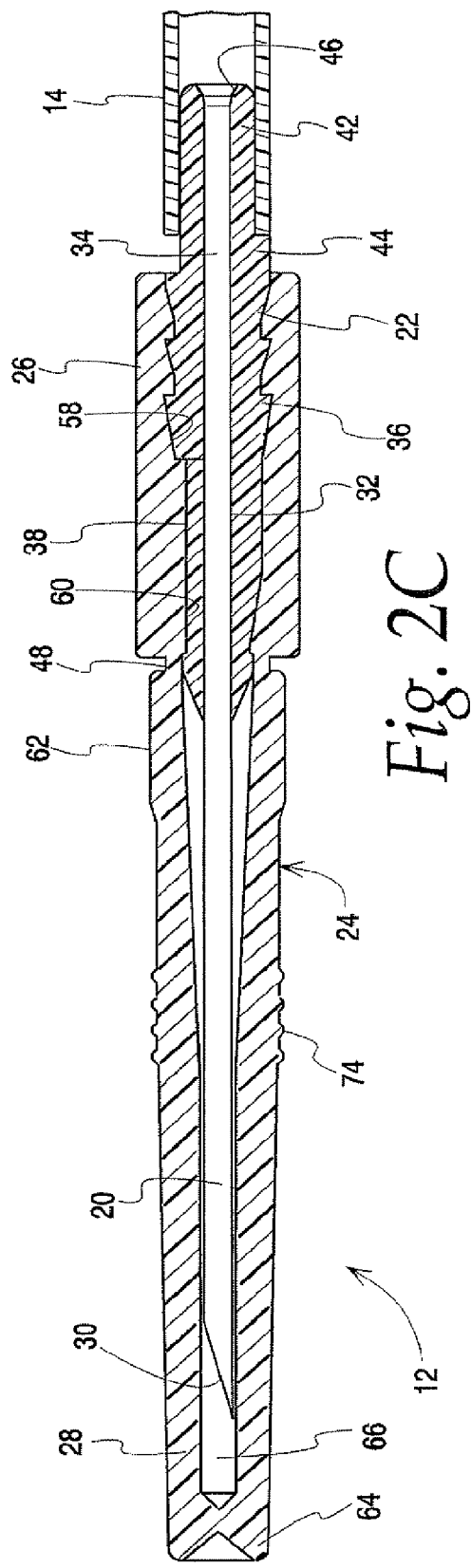
Fig. 2B
Fig. 2C

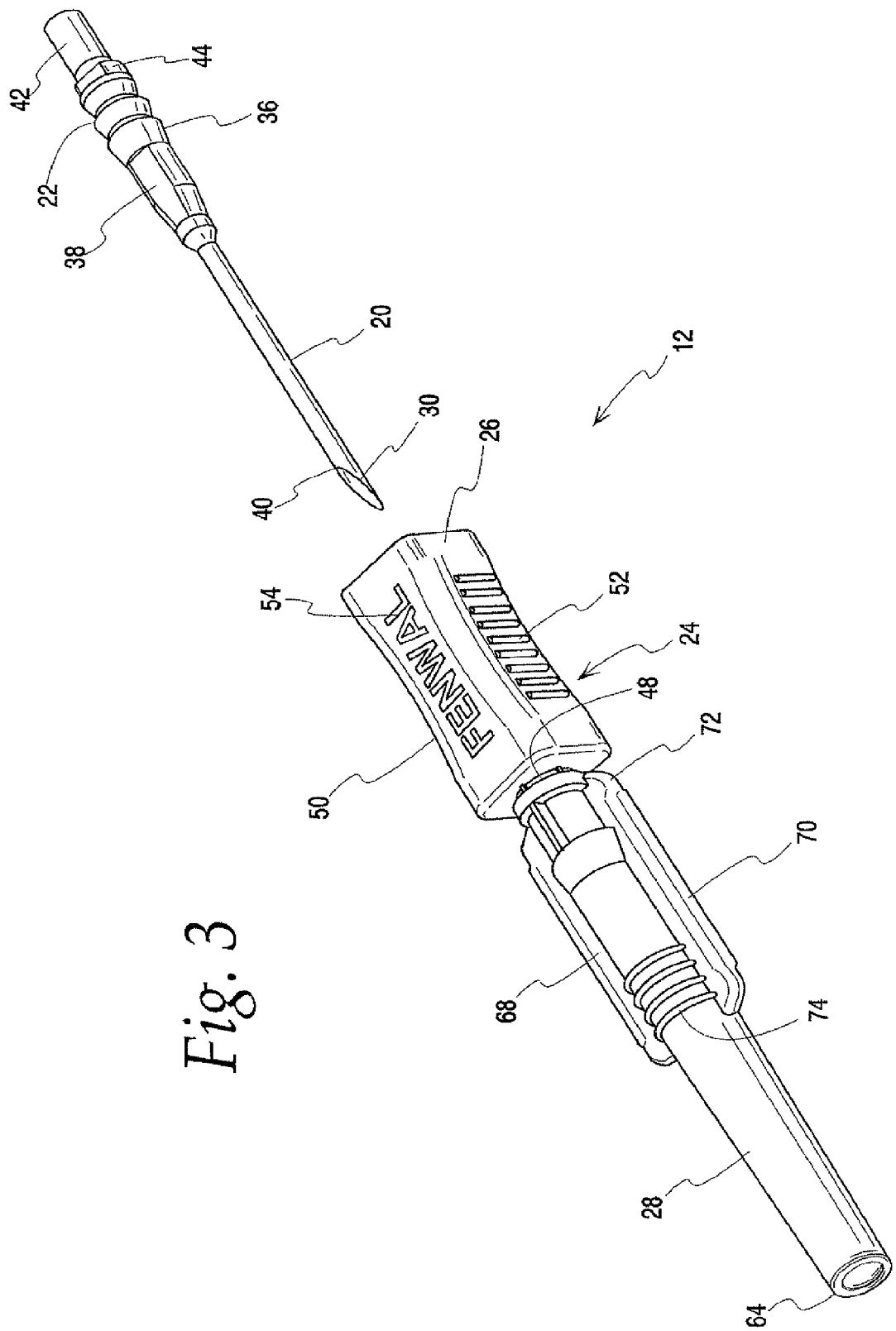

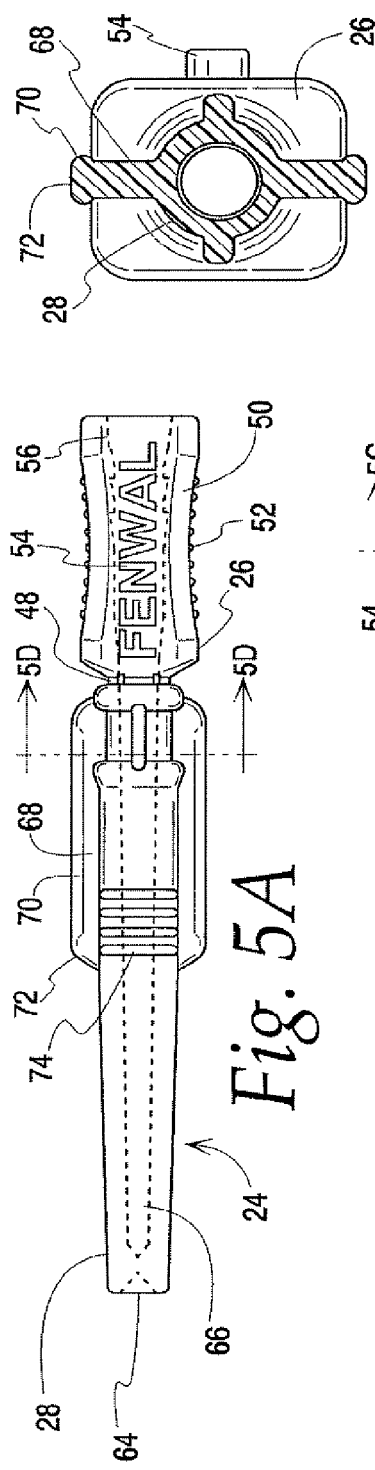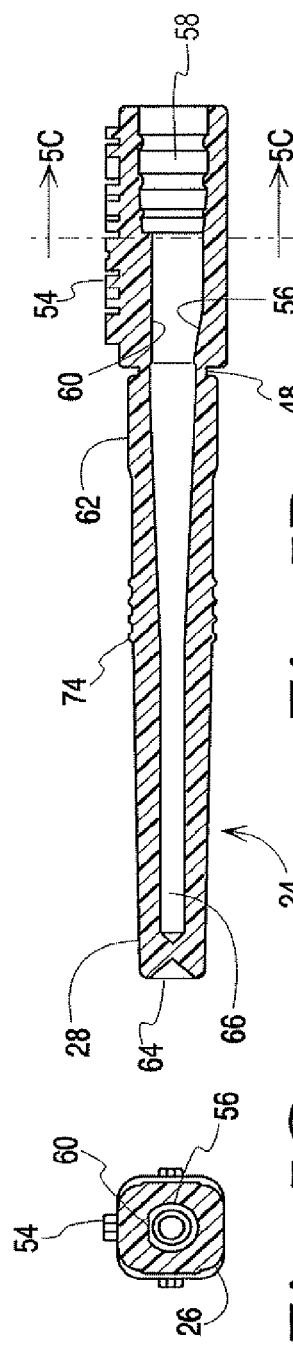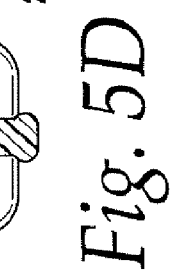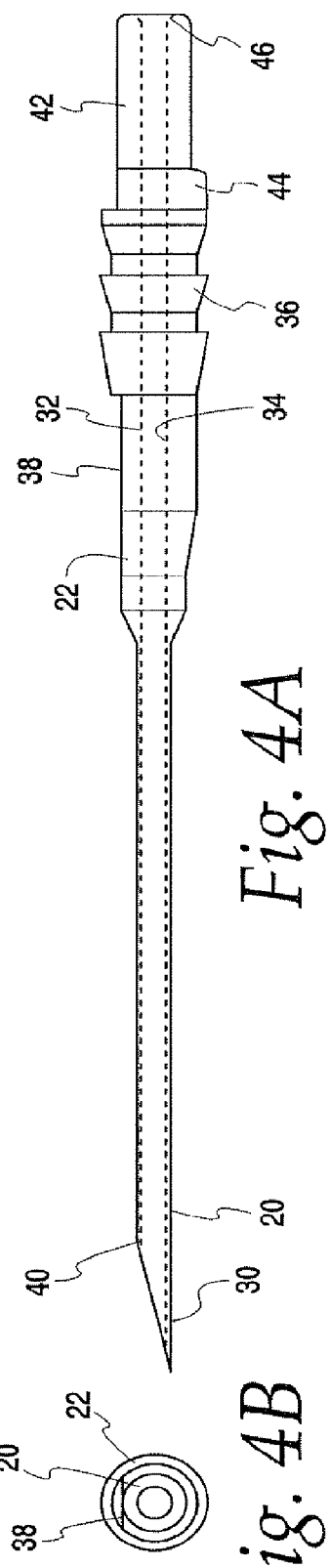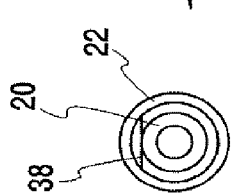

PHLEBOTOMY NEEDLE ASSEMBLY AND FRANGIBLE COVER

The present application is a divisional application of U.S. patent application Ser. No. 12/013,844, filed on Jan. 14, 2008 and issued as U.S. Pat. No. 8,323,251 on Dec. 4, 2012, which is hereby incorporated herein by reference in its entirety.

BACKGROUND

1. Field of the Disclosure

The present subject matter relates to a medical needle assembly of the type commonly used in blood collection or withdrawal systems. More particularly, the present disclosure relates to a needle cover for use in a medical needle assembly according to the foregoing recitation.

2. Description of Related Art

Blood collection sets, in their most basic form, typically include a collection container for receiving blood from a donor and a tube that provides a flow path from the blood donor to the collection container, the tube terminating in a needle for withdrawal of blood from a donor or patient. The needle assembly typically includes a needle or cannula attached to a needle hub which allows for manipulation of the needle assembly by the phlebotomist, nurse, or other medical professional.

Such needles are commonly shielded with a removable needle cover. Shielding the needle protects the medical professional from inadvertent contact with the sharpened needle tip. Shielding the needle also protects the needle from damage during shipping and transport. Shielding also preserves the sterility of the needle prior to use and ideally maintains the integrity of a closed blood collection system by preferably providing a hermetic seal between the needle cover and needle assembly. The needle cover may also optionally provide assurance to the end user that the needle has not been tampered with.

Examples of needle assemblies including associated needle covers are provided in U.S. Pat. Nos. 4,402,682 and 4,496,352, both of which are hereby incorporated herein by reference. These patents disclose a needle assembly including a cannula attached to a base and to donor tubing. The needle covers are made of a plastic material, which forms a thermal bond with the base to provide a tamper evident seal. The needle covers described in the above-referenced patents also include an internal plug within the bore of the needle cover and located at the distal end of the needle cover. The plug is made of a resilient material and includes a pocket for enveloping and protecting the distal needle tip.

Another example of a needle assembly and associated needle cover is disclosed in U.S. Pat. No. 4,551,138, which is hereby incorporated herein by reference. The needle cover disclosed therein includes a hollow body made of a sterilizable plastic material. The needle cover includes a resilient "layer" made of a polymeric elastomer located near the proximal open end of the needle cover. The diameter of the cylindrical resilient layer at the proximal end of the cover has a diameter that is smaller than the diameter of the needle post engaged by the needle cover. The needle cover is placed over the needle and engages the post of the needle hub. According to U.S. Pat. No. 4,551,138, a hermetic seal is formed between the needle cover and the hub or post portion of the needle assembly.

SUMMARY

There are several aspects of the present subject matter which may be embodied in the devices and systems described and claimed below. These aspects may be employed alone or in combination with other aspects of the subject matter described herein.

In one aspect, a needle cover is provided for a medical needle assembly of the type having a base and a cannula. The needle cover comprises a proximal hub portion adapted to be secured to the base and a distal cap portion adapted to substantially enclose at least a distal end of the cannula when the hub portion is secured to the base. The needle cover also includes a frangible portion proximal the cap portion and adapted to be broken to separate the cap portion, allowing removal thereof to expose the distal end of the cannula. The hub portion, the cap portion, and the frangible portion are integrally formed and comprise a plastic material having a hardness in the range from about 35 to about 65 on the Shore D durometer scale, a torsional modulus in the range from about 30 to about 80 MPa, and a Young's modulus in the range from about 15 to about 260 MPa.

In another separate aspect, a needle cover is provided for a medical needle assembly of the type having a base and a cannula. The needle cover comprises a hub portion adapted to be secured to the base and a cap portion adapted to substantially enclose at least a distal end of the cannula when the hub portion is secured to the base. The cap portion comprises at least one generally outwardly extending wing having an outer edge and an enlarged rib adjacent to and/or defining at least a portion of the outer edge of the wing. The cap portion is separable from the hub portion upon application of a torsional force between the hub portion and the cap portion, and the rib of the wing is configured to assist gripping during application of such torsional force.

In a further separate aspect, a needle cover is provided for a medical needle assembly of the type having a base and a cannula. The needle cover comprises a proximal hub portion adapted to be secured to the base and a distal cap portion adapted to substantially enclose at least a distal end of the cannula when the hub portion is secured to the base. At least part of the hub portion and at least part of the cap portion are translucent.

In yet another separate aspect, a needle cover is provided for a medical needle assembly of the type having a base and a cannula. The needle cover comprises a proximal hub portion adapted to be secured to the base and a distal cap portion adapted to substantially enclose at least a distal end of the cannula when the hub portion is secured to the base. The cap portion comprises at least one generally outwardly extending wing having an outer edge and an enlarged rib adjacent to and/or defining at least a portion of the outer edge of the wing. There is a frangible portion proximal the cap portion and adapted to be broken upon application of a torsional force between the hub portion and the cap portion, wherein the rib of the wing is configured to assist gripping during application of such torsional force. The hub portion, the cap portion, and the frangible portion are integrally formed and comprise a substantially transparent plastic material having a hardness in the range from about 35 to about 65 on the Shore D durometer scale, a torsional modulus in the range from about 30 to about 80 MPa, and a Young's modulus in the range from about 15 to about 260 MPa.

BRIEF DESCRIPTION OF THE DRAWINGS

FIG. 1 is a plan view of a disposable blood collection kit;

FIG. 2B is a top plan view of the medical needle assembly of FIG. 2A;

FIG. 2C is a cross-sectional side view of the medical needle assembly of FIG. 2B, taken through the line 2C-2C;

FIG. 3 is an exploded view of another medical needle assembly incorporating a needle cover according to an aspect of the present subject matter;

FIG. 4A is a side view of a cannula and base of a medical needle assembly suitable for use with needle covers according to the present subject matter;

FIG. 4B is an end view of the cannula and base of FIG. 4A;

FIG. 5A is a top plan view of a needle cover according to an aspect of the present subject matter;

FIG. 5B is a cross-sectional side view of the needle cover of FIG. 5A;

FIG. 5C is a cross-sectional end view of the needle cover of FIG. 5A, taken through the line 5C-5C; and FIG. 5D is a cross-sectional end view of the needle cover of FIG. 5A, taken through the line 5D-5D.

DESCRIPTION OF THE ILLUSTRATED EMBODIMENTS

Figure 2A:
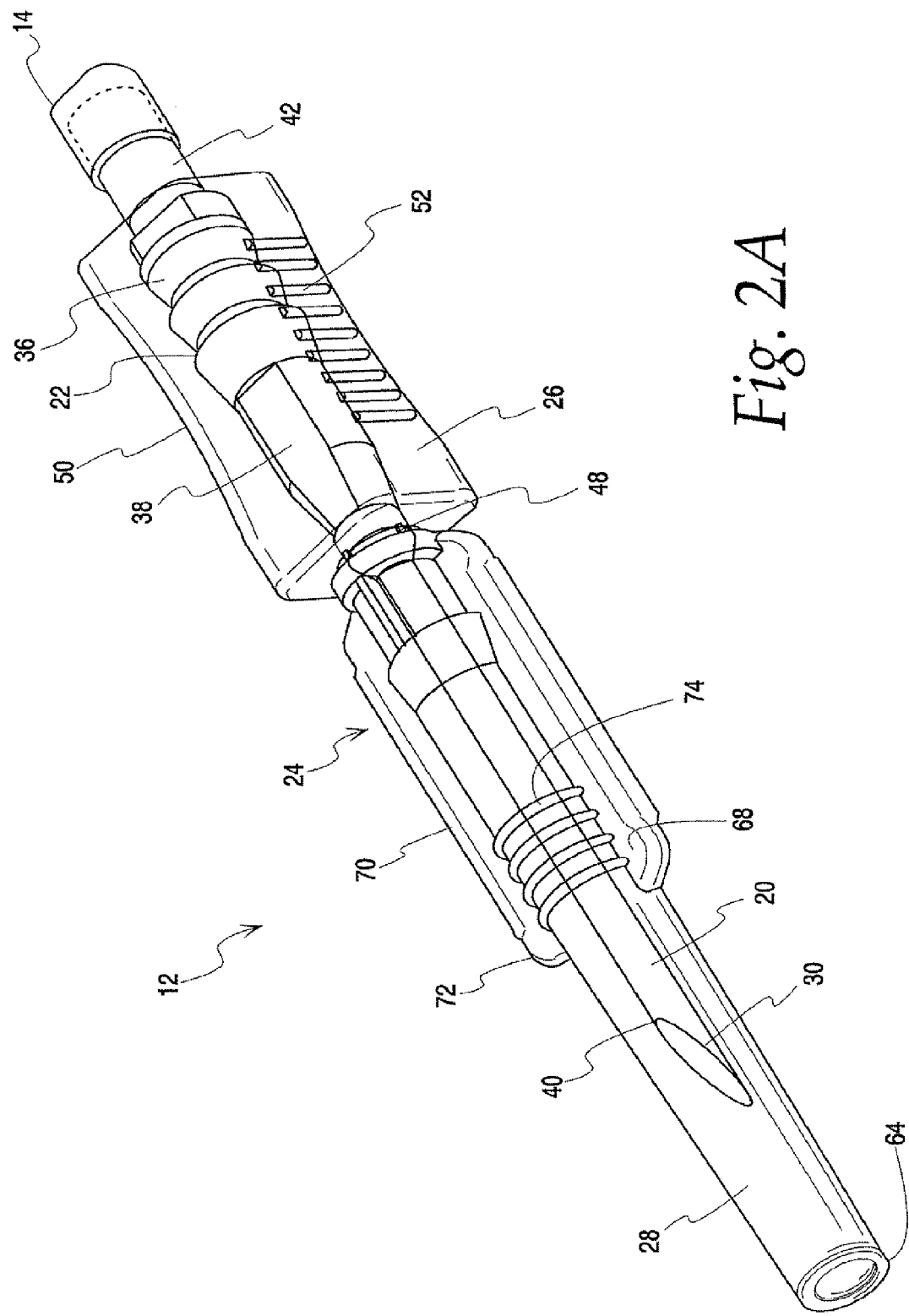
FIG. 2A is a perspective view of a medical needle assembly incorporating a needle cover according to an aspect of the present subject matter.

The embodiments disclosed herein are for the purpose of providing the required description of the present subject matter. These embodiments are only exemplary, and may be embodied in various forms. Therefore, specific details disclosed herein are not to be interpreted as limiting the subject matter as defined in the accompanying claims.

FIG. 1 shows a disposable blood collection and processing kit of the type commonly used in whole blood donations. The disposable set 10 includes a medical needle assembly 12 attached to tubing 14, which provides a flow path to a collection container 16. The disposable set 10 may further include satellite containers 18 for receiving separated blood components and/or for holding a storage medium for a separated component, as will be recognized by those of skill in the art. The system shown in FIG. 1 is just one example of a blood collection processing set. Other examples are shown and described in, for example, U.S. Patent Application Publication No. 2005/0148993, which is hereby incorporated herein by reference.

FIGS. 2A-2C show a medical needle assembly 12 embodying various aspects of the present subject matter. An exploded view of a similar medical needle assembly 12 is shown in FIG. 3. The assembly 12 includes a cannula or needle 20, a base 22 secured to the cannula 20, and a needle cover 24. The cannula 20 is secured to the base 22, and the base 22 is received within a hub portion 26 of the needle cover 24, and a cap portion 28 of the needle cover 24 encloses at least a beveled distal end 30 of the cannula 20. The cap portion 28 is removed to allow access to the cannula 20 and subsequent phlebotomy of a donor or patient.

The cannula 20 (shown more particularly in FIGS. 3-4B) is adapted for insertion into the vein of the blood donor. The cannula 20 is typically made of stainless steel or other suitable alloy metal. The cannula 20 may be further coated by one or more lubricants to facilitate venipuncture. Needle lubricants include, but are not limited to cross-linked, silicone-based lubricants and/or simple lubricating oils that will be known to those of ordinary skill in the art. As seen in FIG. 2C, the cannula 20 is hollow and terminates at its distal end in a sharpened and beveled tip 30.

The cannula 20 is attached to a post or base 22. The base 22 is a generally tubular member that includes a bore 32 (FIG. 2C) for receiving the proximal end or shank 34 of the cannula 30. In one embodiment, the base 22 may be attached to the cannula 20 by overmolding over the proximal end 34 of the cannula. In another embodiment, the proximal end 34 of the cannula 20 may be inserted into the hollow bore 32 of the base 22 and secured by adhesive bonding or other known techniques. Suitable adhesives include, without being limited to, those that are curable by ultraviolet (UV) radiation. Other ways of combining or otherwise attaching the cannula 20 and the base 22, such as by a press-fit, may also be employed without departing from the scope of the present description.

As shown in FIGS. 3 and 4A, the illustrated base 22 includes a plurality of generally frusto-conical, radially extending rings or barbs 36, which interact with the needle cover 24 to secure the base 22 to the needle cover 24, as will be described in greater detail herein. It will be seen in FIGS. 3-4B that the region of the base distal of the barbs 36 includes a flat portion 38. In the illustrated configuration, the base 22 is secured to the cannula 20 such that the flat portion 38 is aligned with the relatively blunt heel 40 of the beveled end 30 of the cannula 20. By such a configuration, the flat portion 38 effectively indicates the orientation of the beveled end 30, which is important for optimal phlebotomy of a donor. As will be described in greater detail herein, the flat portion 38 also serves the further function of ensuring a particular orientation of the beveled end 30 with respect to the needle cover 24 to optimize phlebotomy of a donor.

The proximal end 42 of the base 22 is adapted to form a liquid-tight connection with tubing 14 for association of the medical needle assembly 12 with a blood collection container or set. The base 22 may include a radial flange or abutment 44 against which the tubing 14 abuts when properly connected, thereby providing a visual indication that the tubing 14 is fully installed. In the illustrated embodiment, as best seen in FIG. 2C, the interior surface 46 of the proximal end 42 is tapered or beveled outwardly to smooth the transition from the cannula 20 to the tubing 14, thereby minimizing the occurrence of "dead zones" that would otherwise allow blood to collect and stagnate.

As for the needle cover 24 (FIGS. 5A-5D), it comprises a proximal hub portion 26 and a distal cap portion 28. In the illustrated embodiments, the hub and cap portions are integrally attached, such as one-piece molded construction, and there is a frangible portion 48 proximal the cap portion 28, being more particularly positioned between the hub portion 26 and the cap portion 28. As will be described in greater detail, the frangible portion 48 is adapted to be broken by the phlebotomist, thereby allowing the cap portion 28 to be separated from the remainder of the needle cover 24 and removed, exposing the distal end of the cannula.

The hub portion 26 is intended to be gripped during use of the medical needle assembly 24, so it may be advantageous for it to be compact and easily manipulated between the fingertips of the phlebotomist. For example, the illustrated hub portions include concave sidewalls 50 which allow for comfortable gripping with the thumb and forefinger. The sidewalls 50 may further include gripping members 52 on the surfaces thereof. The gripping members 52 may be molded or embossed projections on the surfaces of the sidewalls 50 that affect the contour thereof. In the illustrated embodiments, the gripping members 52 are configured as spaced apart raised ribs on the sidewalls 50. An enhanced gripping surface can also be provided by other means, such as by treating the sidewalls to make them coarser or less smooth.

Other hub portion configurations may also be employed without departing from the scope of the present subject matter. For example, U.S. Patent Application Publication No.

2006/0089599, which is hereby incorporated herein by reference, shows and describes a number of alternative hub portion configurations.

In one embodiment, which is shown in FIGS. 5A-5C, the outer surface of the hub portion 26 include an indicia 54, which extends generally longitudinally along the length of the hub portion 26. The indicia 54 may take any of a number of forms, but is distinguishable from the rest of the hub portion 26 to function as a reference point for the proper alignment of the beveled end 30 of cannula 20 during assembly and use, as will be described in greater detail herein.

The hub portion 26 includes an inner bore 56 (FIGS. 2C and 5B) for receiving the base 22, which is itself secured to the cannula 20. The inner bore 56 is configured to substantially correspond to the shape of the outer surface of the base 22, such that there is a relatively tight fit when the base 22 is pressed into the bore 56 (FIG. 2C). In particular, the illustrated inner bore 56 includes annular notches, grooves, or recesses 58 corresponding to the barbs 36 of the base 22 and a flat portion 60 (shown in FIGS. 5B and 5C) corresponding to the flat portion 38 of the base 22. When the base 22 is inserted into the hub portion 26 (moving the combined cannula 20 and base 22 from right-to-left in the orientation of FIG. 3), the flat portions 38 and 60 must be aligned to allow the base 22 to be fully inserted. With the flat portions 38 and 60 so aligned, the base 22 can be fully inserted into the inner bore 56 of the hub portion 26, with the barbs 36 seating within the associated annular notches 58, thereby preventing subsequent removal of the base 22 and cannula 20 from the hub portion 26.

As described above, the respective flat portions 38 and 60 of the base 22 and the hub portion 26 must be aligned for the base 22 to be fully inserted within the inner bore 56 of the hub portion 26. In the illustrated embodiments, the flat portion 60 of the hub portion 26 is aligned with the indicia 54 on the outer surface of the hub portion 26, while the flat portion 38 of the base 22 is aligned with the heel 40 of the beveled end 30 of the cannula 20. Therefore, alignment of the flat portions 38 and 60 effectively aligns the indicia 54 and the heel 40. It will be appreciated that, by such a configuration, the indicia 54 acts as a bevel indicator and a phlebotomist can ascertain the orientation of the beveled end 30 of the cannula 20 by simply referring to the position of the indicia 54 on the hub portion 26.

Turning now to the cap portion 28, the illustrated embodiment is tapered as it extends from an open proximal end 62 adjacent to the hub portion 26 to a closed distal end 64. An inner cavity 66 of the cap portion 28 (FIGS. 2C and 5B) is sized to receive and substantially enclose at least the beveled distal end 30 and preferably the entire exposed length of the cannula 20 when the base 22 has been fully inserted into the inner bore 56 of the hub portion 26. In the embodiment illustrated in FIG. 2C, there is preferably spacing or separation between the surface of the inner cavity 66 and the cannula 20, which may be advantageous in preventing the sharp tip 30 of the cannula 20 from contacting and damaging the cap portion 28 during assembly.

The outer surface of the cap portion 28 may include at least one outwardly extending wing 68. The illustrated cap portion 28 defines a central longitudinal axis and a pair of wings 68 extending generally radially away from the central axis. In one embodiment, the wings 68 extend away from the central axis in generally opposite directions, such that they are substantially coplanar. Rising above the surface of each wing 68 is an enlarged rib 70 (FIGS. 5A and 5D) that is adjacent to and/or defines at least a portion of an outer edge 72 of the associated wing 68. The illustrated enlarged ribs 70 are substantially parallel to the central axis of the cap portion 28. As will be described in greater detail, the cap portion 28 may be separated from the remainder of the needle cover 24 by application of a torsional force, and enlarged ribs according to the illustrated configuration may be advantageous for application of such torsional force. The cross-sectional surface (FIG. 5D) of each enlarged rib 70 may be curved or otherwise configured to provide a surface that is more comfortably gripped by the phlebotomist during application of such torsional force.

The cap portion 28 may also include at least one annular raised rib 74 that is positioned in a plane substantially perpendicular to the central axis. In the illustrated embodiments, the cap portion 28 includes a plurality of annular ribs 74 that are longitudinally spaced from each other. As will be described in greater detail herein, after breaking of the frangible portion 48, the cap portion 28 is moved distally to separate it from the remainder of the needle cover 24, thereby exposing the beveled distal end 30 of the cannula 20, and the annular ribs 74 function to provide a gripping surface when so removing the cap portion 28.

As for the frangible portion 48, it may be provided as a relatively weak section proximal the cap portion 28. In the illustrated embodiments, the frangible portion 48 is provided as a necked-down section of relative thin thickness intermediate the cap portion 28 and the hub portion 26. In accordance with the foregoing description, the cap portion 28 is adapted to be separated and removed from the remainder of the needle cover 24, and the frangible portion 48 is broken to allow the cap portion 28 to be so removed.

In one embodiment, the frangible portion 48 is adapted to break upon application of a torsional force. Such force is typically applied by gripping the hub portion 26 with one hand, gripping the cap portion 28 with another hand, and rotating the hub portion 26 and the cap portion 28 in opposite directions about the central axis defined by the cap portion 28. As described above, the wings 68 and (in particular) the enlarged ribs 70 are configured to be gripped during application of such torsional force, and it will be appreciated that positioning each enlarged rib 70 at the outer edge 72 of the associated wing 68 provides for a relatively large moment arm, thereby decreasing the force that must be applied by the phlebotomist to break the frangible portion 48. To minimize user discomfort, it may be further advantageous to provide a frangible portion 48 that is adapted to break upon application of a torsional force in the range from about 2 to about 24 in-ounces and upon less than about 90° relative rotation between the hub portion 26 and the cap portion 28. Additionally, as shown in FIG. 2C, it may be advantageous for there to be a slight friction fit between the distal end of the base 22 and the inner surface of the frangible portion 48 or the proximal end 62 of the cap portion 28 to prevent the cap portion 28 from falling off when the frangible portion 48 is broken. If provided, the raised annular ribs 74 on the cap portion 28 may be gripped to pull the cap portion 28 and overcome such friction fit.

The hub portion 26, cap portion 28, and frangible portion 48 may be integrally formed or, as in one embodiment, molded as a single piece. If so configured, it may be advantageous to construct the needle cover 24 from a material that: (1) is sufficiently rigid to minimize the bending of the underlying cannula 20, (2) is suitable for allowing the frangible portion 48 to be broken under the aforementioned conditions, and/or (3) has a moisture vapor transmission rate sufficient for steam sterilization of the beveled distal end 30 of the cannula 20 when it is enclosed by the cap portion 28 (e.g., a moisture vapor transmission rate in the range from about 30 to about 90 g/m$^2$/day at approximately 38° C. at 100% relative humidity). More particularly, it may be advantageous to make the hub, cap, and frangible portions of a plastic material, such as a material having a hardness in the range from about 35 to about 65 on the Shore D durometer scale, a torsional modulus in the range from about 30 to about 80 MPa, and/or a Young's modulus in the range from about 15 to about 260 MPa. Even more particularly, it may be advantageous to provide a plastic material having a hardness less than 55 on the Shore D durometer scale. More particularly still, it may be advantageous to provide a plastic material having a hardness of about 47 on the Shore D durometer scale.

An additional property that may be advantageous for the needle cover material to possess is translucence or, even more advantageously, substantial transparency. Such a material allows the beveled distal end of the cannula to be seen through the cap portion and allows the base to be seen through the hub portion (FIGS. 2A and 2B). This allows the cannula and base to be visually inspected following assembly to assure that there has been no damage thereto during assembly.

One plastic material that has been found to possess these advantageous characteristics is the polyamide material marketed under the name VESTAMID® E47-S1 by Evonik Degussa GmbH of Essen, Germany. However, those of ordinary skill in the art will recognize that other materials may also be used, particularly if performance characteristics different from those recited herein are desired.

In other embodiments, the various sections of the needle protector may be comprised of different materials. For example, the hub portion may be formed from a softer material than the cap portion to provide different tactile and handling characteristics. Further, the construction of any portion of the needle protector is not limited to a single material. For example, the hub portion or the cap portion could include one or more sections formed from a material having a particular rigidity or translucence or transparency and one or more other sections formed from another material having different characteristics.

Medical needle assemblies according to the foregoing description have particular applicability to blood collection and processing systems. For example, it is contemplated that such a medical needle assembly could be incorporated into any of the various Blood-Pack® Units marketed by Fenwal, Inc. of Lake Zurich, Ill. However, needle assemblies according to the foregoing description are not limited to a particular use or range of uses and it is contemplated that such medical needle assemblies could be incorporated in any system and assembly involving needle entry into the vascular system of a patient or donor.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A medical needle assembly, comprising:
   a cannula;
   a base secured to a proximal end of the cannula and including at least one base retention member; and
   a needle cover comprising
      a proximal hub portion including an inner bore with at least one hub retention member which mates with said base retention member to secure the hub portion to the base;
      a distal cap portion substantially enclosing at least a distal end of the cannula; and
      a frangible portion proximal the cap portion and adapted to be broken to separate the cap portion, allowing removal thereof to expose the distal end of the cannula,
   characterized in that
   the base includes separate, substantially co-planar flat portions positioned adjacent to the base retention member, with the base including only one flat portion positioned proximally of the base retention member and only one flat portion positioned distally of the base retention member,
   the distal end of the cannula includes a heel aligned with said flat portions of the base, and
   at least part of one of said flat portions extends outside of the inner bore of the hub portion and is indicative of the orientation of the heel.

2. The medical needle assembly of claim 1, wherein the base includes a substantially tubular proximal end positioned proximally to said flat portions.

3. The medical needle assembly of claim 1, wherein the base is overmolded onto the proximal end of the cannula.

4. The medical needle assembly of claim 1, wherein the base is adhered to the proximal end of the cannula.

5. The medical needle assembly of claim 1, wherein the base is press-fit onto the proximal end of the cannula.

6. The medical needle assembly of claim 1, wherein the flat portions of the base are substantially aligned with each other.

7. The medical needle assembly of claim 1, wherein the inner bore of the hub portion includes a flat portion aligned with the heel of the cannula and with said flat portions of the base and positioned in facing relation to at least one of the flat portions of the base.

8. The medical needle assembly of claim 1, wherein the hub portion includes an external indicia aligned with the heel of the cannula and with said flat portions of the base.

9. The medical needle assembly of claim 1, wherein the inner bore of the hub portion includes a flat portion aligned with the heel of the cannula and with said flat portions of the base and positioned in facing relation to at least one of the flat portions of the base and wherein the hub portion includes an external indicia aligned with the heel of the cannula and with said flat portions of the base.

10. The medical needle assembly of claim 1, wherein each flat portion is present in a plane that is non-orthogonal to a central axis of the cannula.

11. The medical needle assembly of claim 1, wherein the base retention member is generally frusto-conical.

12. A medical needle assembly, comprising:
   a cannula;
   a base secured to a proximal end of the cannula and including at least one base retention member; and
   a needle cover comprising
      a proximal hub portion including an inner bore with at least one hub retention member which mates with said base retention member to secure the hub portion to the base;
      a distal cap portion substantially enclosing at least a distal end of the cannula; and
      a frangible portion proximal the cap portion and adapted to be broken to separate the cap portion, allowing removal thereof to expose the distal end of the cannula,
   characterized in that
   the base includes separate flat portions positioned adjacent to the base retention member, wherein the base includes only one flat portion positioned proximally of the base retention member and only one flat portion positioned distally of the base retention member and each flat portion is present in a plane that is non-orthogonal to a central axis of the cannula, the distal end of the cannula includes a heel aligned with said flat portions of the base, and at least part of one of said flat portions extends outside of the inner bore of the hub portion and is indicative of the orientation of the heel.

13. The medical needle assembly of claim 12, wherein the base retention member is generally frusto-conical.

14. The medical needle assembly of claim 12, wherein the base includes a substantially tubular proximal end positioned proximally to said flat portions.

15. The medical needle assembly of claim 12, wherein the flat portions of the base are substantially aligned with each other.

16. A medical needle assembly, comprising:

a cannula;

a base secured to a proximal end of the cannula and including at least one base retention member; and a needle cover comprising a proximal hub portion including an inner bore with at least one hub retention member which mates with said base retention member to secure the hub portion to the base;

a distal cap portion substantially enclosing at least a distal end of the cannula; and a frangible portion proximal the cap portion and adapted to be broken to separate the cap portion, allowing removal thereof to expose the distal end of the cannula, characterized in that the base includes flat portions positioned adjacent to the base retention member, wherein the base includes only one flat portion positioned proximally of the base retention member and only one flat portion positioned distally of the base retention member and the base retention member is generally frusto-conical and separates the flat portions, the distal end of the cannula includes a heel aligned with said flat portions of the base, at least part of one of said flat portions extends outside of the inner bore of the hub portion and is indicative of the orientation of the heel, and the flat portions are substantially co-planar and/or are each present in a plane that is non-orthogonal to a central axis of the cannula.

17. The medical needle assembly of claim 16, wherein the base includes a substantially tubular proximal end positioned proximally to said flat portions.

18. The medical needle assembly of claim 16, wherein the flat portions of the base are substantially aligned with each other.

* * * * *